US011896698B2

(12) United States Patent
Wilson et al.

(10) Patent No.: US 11,896,698 B2
(45) Date of Patent: Feb. 13, 2024

(54) PERSONAL CLEANSING COMPOSITIONS AND METHODS OF STABILIZING THE MICROBIOME

(71) Applicant: RB HEALTH (US) LLC, Parsippany, NJ (US)

(72) Inventors: Jessica Wilson, Montvale, NJ (US); Sarah Frances de Szalay, West Milford, NJ (US); Elizabeth Bruning, Berkeley Heights, NJ (US); Rui Yang, Fair Lawn, NJ (US)

(73) Assignee: RB Health (US) LLC, Parsippany, NJ (US)

( * ) Notice: Subject to any disclaimer, the term of this patent is extended or adjusted under 35 U.S.C. 154(b) by 1210 days.

(21) Appl. No.: 15/763,920

(22) PCT Filed: Sep. 30, 2016

(86) PCT No.: PCT/GB2016/000175
§ 371 (c)(1),
(2) Date: Mar. 28, 2018

(87) PCT Pub. No.: WO2017/055789
PCT Pub. Date: Apr. 6, 2017

(65) Prior Publication Data
US 2019/0053993 A1 Feb. 21, 2019

Related U.S. Application Data

(60) Provisional application No. 62/235,716, filed on Oct. 1, 2015.

(51) Int. Cl.
| | | |
|---|---|---|
| A61K 8/44 | (2006.01) | |
| A61K 8/34 | (2006.01) | |
| A61K 8/365 | (2006.01) | |
| A61K 8/46 | (2006.01) | |
| A61Q 17/00 | (2006.01) | |
| A61Q 19/10 | (2006.01) | |
| A61K 8/45 | (2006.01) | |
| A61K 8/20 | (2006.01) | |
| A61K 31/095 | (2006.01) | |
| A61K 8/86 | (2006.01) | |
| A61Q 19/00 | (2006.01) | |

(Continued)

(52) U.S. Cl.
CPC .............. *A61K 8/442* (2013.01); *A61K 8/046* (2013.01); *A61K 8/20* (2013.01); *A61K 8/345* (2013.01); *A61K 8/365* (2013.01); *A61K 8/39* (2013.01); *A61K 8/42* (2013.01); *A61K 8/44* (2013.01); *A61K 8/45* (2013.01); *A61K 8/463* (2013.01); *A61K 8/86* (2013.01); *A61K 31/047* (2013.01); *A61K 31/095* (2013.01); *A61K 31/19* (2013.01); *A61K 31/765* (2013.01); *A61K 31/785* (2013.01); *A61K 45/06* (2013.01); *A61Q 17/005* (2013.01); *A61Q 19/005* (2013.01); *A61Q 19/10* (2013.01); *A61K 2800/75* (2013.01)

(58) Field of Classification Search
CPC . A61K 8/442; A61K 8/45; A61K 8/20; A61K 31/095; A61K 8/86; A61K 8/39; A61K 31/19; A61K 31/765; A61K 8/046; A61K 31/785; A61K 8/44; A61K 31/047; A61K 45/06; A61K 8/42; A61K 8/345; A61K 8/365; A61K 8/463; A61K 2800/75; A61K 31/205; A61Q 19/005; A61Q 17/005; A61Q 19/10; A61P 31/10; A61P 31/04; A61P 31/02; A61P 17/16; A61P 17/00; A61P 15/02
See application file for complete search history.

(56) References Cited

U.S. PATENT DOCUMENTS

| | | |
|---|---|---|
| 2004/0204492 A1 | 10/2004 | Shroot et al. |
| 2004/0265264 A1 | 12/2004 | Sugar et al. |

(Continued)

FOREIGN PATENT DOCUMENTS

| | | |
|---|---|---|
| CN | 101262842 A | 9/2008 |
| CN | 101686916 A | 3/2010 |

(Continued)

OTHER PUBLICATIONS

Yoo-Kyung Lee et al., *Vaginal pH-Balanced Gel for the Control of Atrophic Vaginitis among Breast Cancer Survivors*, 117(4) Obstetrics & Gynecology, 922-27 (2011).*
Joseph Fowler, *Understanding the Role of Natural Moisturizing Factor in Skin Hydration*, 9 Practical Dermatology, 36-40 (2012).*
"Ionic Liquid and Nonionic or Anionic Surfactant—Containing Antimicrobial Compositions," ip.com Journal, ip.com Inc., Jul. 22, 2008, XP013125859.

(Continued)

*Primary Examiner* — Snigdha Maewall
(74) *Attorney, Agent, or Firm* — Dunlap Codding, P.C.

(57) ABSTRACT

A personal wash composition which provides an effective antimicrobial benefit against fungi, gram positive and gram negative bacteria, which composition comprises: a) from 0.1% to 10 wt % betaine surfactant, b) from 0.1% to 5.0 wt % lactic acid, c) from 0.1% to 20 wt % polyhydric $C_2$-$C_6$ alcohol, d) from 0% to 10 wt % alkyl polyethoxy carboxylate of the formula $RO(CH_2CH_2O)_kCH_2COO^-M^+$ wherein R is a $C_8$-$C_{22}$ alkyl, k is an integer from 0 to 20, and M is a soluble salt-forming cation, e) from 0% to 10 wt % alkyl polyethoxy amides of the formula $RO(CH_2CH_2O)_kCH_2CONH_2$ wherein R is a $C_8$-$C_{22}$ alkyl, k is an integer from 0 to 20, f) >8 wt % alkyl ether sulphate, g) water, h) a pH of 3.8-4.5, i) 10-20 wt % total surfactant, j) from 0.1 to 10 wt % metal salt.

16 Claims, No Drawings

(51) Int. Cl.
    *A61K 8/39*     (2006.01)
    *A61K 31/19*     (2006.01)
    *A61K 31/765*     (2006.01)
    *A61K 8/04*     (2006.01)
    *A61K 31/785*     (2006.01)
    *A61K 31/047*     (2006.01)
    *A61K 45/06*     (2006.01)
    *A61K 8/42*     (2006.01)

(56) References Cited

U.S. PATENT DOCUMENTS

| | | |
|---|---|---|
| 2007/0247960 A1 | 10/2007 | Minzoni et al. |
| 2008/0247960 A1 | 10/2008 | Yuan |
| 2010/0210499 A1 | 8/2010 | Allef et al. |
| 2015/0118328 A1 | 4/2015 | Castán Barberán et al. |

FOREIGN PATENT DOCUMENTS

| | | |
|---|---|---|
| CN | 104352358 A | 2/2015 |
| EP | 1593371 A1 | 5/2004 |
| EP | 1593371 A1 | 11/2005 |
| ES | 2334746 A1 | 3/2010 |
| JP | 2004512346 A | 4/2004 |
| PL | 396256 A1 | 3/2013 |
| WO | 2002/036081 A2 | 5/2002 |
| WO | 2007031756 A1 | 3/2007 |
| WO | 2014116106 A1 | 7/2014 |
| WO | 2014201541 A1 | 12/2014 |
| WO | 2015138479 A1 | 9/2015 |

OTHER PUBLICATIONS

Database WPI, Week 201345, Mar. 18, 2013, Thomson Scientific, XP002764611, "Intimate hygiene wash, Intimate cleanser, comprises surfactant, wetting agent, pH regulator, preservative, antibacterial substance, complexing agent and demineralized water, where complexing agent is in form of tetrasodium EDT", & PL 396 256 AI (OCEANIC SA) abstract.
Database GNPD [Online] MINTEL; Jul. 31, 2015, Anonymous: "Intimate hygiene gel", XP002764612, Database accession No. 3289391, p. 2.
Database GNPD [Online] MINTEL; Aug. 30, 2015 (Aug. 30, 2015), Anonymous: "Intimate sensitive gel", XP002764613, Database accession No. 3482335, p. 2.
Database GNPD [Online] MINTEL; Mar. 31, 2008, Anonymous: "Mousse", XP002769251, Database accession No. 882370, p. 1-p. 2.
International Search Report and Written Opinion issued in International Application No. PCT/GB2016/000175 dated Apr. 25, 2017.
Notice of Reason for Refusal Office Action mailed in co-pending Japanese Patent Application No. JP2018516671.

\* cited by examiner

PERSONAL CLEANSING COMPOSITIONS AND METHODS OF STABILIZING THE MICROBIOME

FIELD OF THE INVENTION

The present invention relates to personal cleansing compositions, which are particularly useful in personal care applications, (e.g. topical skin care, cleansing including most preferably feminine intimate hygiene products), which compositions exhibit an appreciable antimicrobial benefit, yet are mild and non-irritating to the skin and provide targeted protection from infection benefits while maintaining the balance of healthy vulvar microbiome.

BACKGROUND OF THE INVENTION

Washing is one of life's fundamental requirements for cleansing in terms of dirt removal and hygiene maintenance.

Daily use of personal hygiene compositions containing certain active agents have been known to cause irritation and drying of the skin, particularly in sensitive/intimate regions of the female body. This both limits the frequency of their use and often times requires the use of corrective skin moisturizers.

Improper hygiene may contribute to odour and vulvovaginal infections and issues for women. Moreover, maintenance of the microbial balance plays a key role in overall vulvovaginal health and protection from pathogens gaining a foothold. Besides harsh antiseptics, factors that disturb the natural pH level of the vulvovaginal area can negatively impact the composition of the natural vulvovaginal microbiome that is needed for protection against infection. Proper intimate hygiene is critically important for feminine health. Use of high pH soaps are not recommended by the Royal College of Obstetricians and Gynaecologists (RCOG) Guidelines and most physicians, because such soaps may cause dryness or other skin issues.

Current products on the market have limited ability to deliver an appropriate level of antibacterial action while others provide too high a level of germ kill for the intimate area and do not provide skin balance/moisturization. Some products use biocides such as triclosan, chlorohexidine or other antiseptics/other harsh chemicals to deliver germ kill. There exists the need in the market for a feminine intimate hygiene formulation which delivers antibacterial action, whilst maintaining a healthy balance of the skin's natural flora, is non-drying to the skin, provides a moisturising benefit, and is suitable for everyday use while at the same time providing protection of the intimate area.

A healthy vagina is dominated by *Lactobacillus*, which is a non-sporing, gram-positive bacilli that produces lactic acid, resulting in an acidic environment (pH 3-4). Vaginal pH correlates with total lactate concentration as the vaginal mucosa is also a rich source of lactic acid, a by-product of estrogen-regulated anaerobic glucose metabolism. The normal vaginal flora, acidic vaginal pH, and vaginal discharge are all components of the innate defense mechanisms that protect against vulvovaginal infections. The importance of vaginal lactic acid needs to be emphasized, as it correlates with vaginal health, inhibits the growth of bacteria associated with bacterial vaginosis, and possibly plays a role in the local immune defense.

Because of the risks associated with internal washing/douching, external feminine washes are considered more appropriate for intimate health, particularly those containing lactic acid, with an acidic pH that augments skin homeostasis and may serve as a helpful adjunct therapy in women with vaginal infections or taking antibiotics.

It is an object of the present invention to obviate or mitigate some of the disadvantages outlined above.

DEFINITION OF THE INVENTION

According to a first aspect of the present invention there is provided a personal wash composition which provides an effective antimicrobial benefit against fungi, gram positive and gram negative bacteria and which also provides mild cleansing to the skin including protection of the commensal microflora of the skin, which composition comprises:
  a) from 0.1 wt % to 10 wt % betaine surfactant,
  b) from 0.1 wt % to 5.0 wt % lactic acid,
  c) from 0.1 wt % to 20 wt % polyhydric $C_2$-$C_6$ alcohol,
  d) from 0 wt % to 10 wt % alkyl polyethoxy carboxylate of the formula
    $RO(CH_2CH_2O)_kCH_2COO^-M^+$ wherein R is a $C_8$-$C_{22}$ alkyl, k is an integer from 0 to 20, and M is a soluble salt-forming cation,
  e) from 0 wt % to 10 wt % alkyl polyethoxy amides of the formula $RO(CH_2CH_2O)_kCH_2CONH_2$ wherein R is a $C_8$-$C_{22}$ alkyl, k is an integer from 0 to 20,
  f) >8 wt % alkyl ether sulphate,
  g) water,
  h) a pH of 3.8-4.5,
  i) 10-20 wt % total surfactant,
  j) from 0.1 to 10 wt % metal salt.

The composition is preferably used as a feminine intimate hygiene product but may also be used widely within personal care or personal cleansing including liquid hand wash, body wash, mild shampoo or body wash for children and infants.

The invention is specially formulated for the external skin and mucous membranes of, e.g., the vulva or intimate area to provide gentle cleansing, freshness, antibacterial protection to maintain healthy balance (particularly of intimate areas).

It delivers four principal benefits: (1) gentle cleansing (2) skin moisturization (3) mild but effective antimicrobial action against transient organisms and (4) commensal microbial balance. This achievement of gentle cleansing with skin moisturisation is significant. Further these aims are achieved at optimal skin pH. Additionally it has been found that the composition of the invention does not disrupt or harm the natural skin flora and promotes balanced flora on a user's skin and furthermore stabilization of the microbiome The composition is preferably in the form of a gel, although the composition may be in different formats. Preferred, non-limiting, examples of different formats include a foam.

According to a second aspect of the present invention there is provided a personal wash composition, in the form of a foam, which provides an effective antimicrobial benefit against gram-positive and gram-negative bacteria, which composition comprises:
  a) from 0.1 wt % to 5 wt % betaine surfactant,
  b) from 0.1 wt % to 5 wt % lactic acid,
  c) from 0.1 wt % to 20 wt % polyhydric $C_2$-$C_6$ alcohol,
  d) water,
  e) a pH of 3.8-4.5,
  f) 0.1-5 wt % total surfactant.

The foam preferably has a density of less than 500 g/litre, more preferably less than 400 g/litre, more preferably less than 300 g/litre and most preferably less than 200 g/litre.

The foam of the second aspect of the invention may be prepared by a user, e.g. in a manual mixing process. Alternatively the foam of the second aspect of the invention may be prepared with the use of a foaming dispenser, such as described in U.S. Pat. No. 6,840,408, the contents of which are incorporated by reference.

The composition in either its gel or foam form has been found to provide excellent creamy foaminess with surprisingly trouble-free rinse ability (removal with water).

Most preferably the use is as a feminine (intimate) wash composition.

When used as a feminine wash formulation it has been found that the composition provides/maximum/optimal antibacterial benefits and furthermore is also gentle and clinically tested to be mild. The rinse-off formulation is also clinically proven to be moisturizing and helps protect from dryness and does not harm the intimate natural microflora.

The invention utilizes a natural, bio-similar active, lactic acid and provides mild antibacterial action at an appropriate pH for this area of the body. The invention further provides balance to the intimate area by sustaining an optimal skin pH, moisturized skin and balanced vaginal flora.

It has been found to prevent key intimate hygiene concerns (infections caused by transient bacteria, B strep, odour, irritation, itching, inflammation, pain, discomfort). Protection against Group B *Streptococcus* is particularly important for pregnant women as it leads to urinary track infections, upper genital tract infections, postpartum endometritis, pneumonia and puerperal sepsis.

Thus according to a third aspect of the present invention there is provided a method for providing a germicidal benefit to a topical surface, especially a dermal surface, the method comprising the step of: contacting a topical surface upon which the presence of one or more undesired pathogens, preferably bacteria, are known or suspected, with a composition according to a first or second aspect of the invention.

The composition of the present invention provides an optimal combination of such properties as antiseptic, i.e., antimicrobial activity, cleansing, conditioning, and moisturizing, together with safety and efficacy, ease of storage and use, and aesthetic properties.

The composition/method of the present invention provides as a primary technical benefit the reduction of undesired microorganisms, particularly in the reduction of both gram positive and gram negative microorganisms, while at the same time providing secondary benefits including skin conditioning and/or skin cleansing. Further ancillary benefits may be provided by the presence of one or more of the optional constituents which may be included in formulations or compositions according to the present intervention.

DETAILED DESCRIPTION OF THE FIRST ASPECT OF THE INVENTION

More preferably the betaine surfactant is present in an amount of from 1-3 wt %, and most preferably about 1.3 wt %.

Alkyl betaines are known surfactants which are mainly produced by carboxyalkylation, preferably carboxymethylation of aminic compounds. Typical examples are the carboxymethylation products of hexyl methyl amine, hexyl dimethyl amine, octyl dimethyl amine, decyl dimethyl amine, dodecyl methyl amine, dodecyl dimethyl amine, dodecyl ethyl methyl amine, $C_{12/14}$ cocoalkyl dimethyl amine, myristyl dimethyl amine, cetyl dimethyl amine, stearyl dimethyl amine, stearyl ethyl methyl amine, oleyl dimethyl amine, $C_{16/18}$ tallow alkyl dimethyl amine and technical mixtures thereof. Alkyl amidobetaines which represent carboxyalkylation products of amidoamines are also suitable. Typical examples are reaction products of fatty acids containing 6 to 22 carbon atoms, namely caproic acid, caprylic acid, capric acid, lauric acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof, with N,N-dimethylaminoethyl amine, N,N-dimethylaminoproply amine, N,N-diethylaminoethyl amine and N,N-diethylaminoproply amine which are condensed with sodium chloroacetate.

Most preferably the betaine comprises cocoamidopropyl betaine.

More preferably the lactic acid is present in an amount of from 0.2-8 wt %, more preferably 0.3-7 wt %, more preferably 0.4-5 wt % and most preferably from 2-5 wt %, e.g. about 2.25 wt %.

More preferably the polyhydric $C_2$-$C_6$ alcohol is present in an amount of 2-18 wt %, more preferably 6-17 wt %, more preferably 8-16 wt %, and most preferably from 10-15 wt %.

Most preferably the polyhydric $C_2$-$C_6$ alcohol comprises glycerol.

Most preferably the alkyl polyethoxy carboxylate is present in an amount of from 2-7 wt %, most preferably about 4.9 wt %

Most preferably in the alkyl polyethoxy carboxylate R comprises a $C_{12}$ alkyl; K is 11 and M is Na.

More preferably the alkyl polyethoxy amide is present in an amount of up to 8 wt %, more preferably up to 5 wt %, more preferably up to 4 wt %, and most preferably up to 3 wt %, More preferably the alkyl polyethoxy amide is present in an amount of greater than 0.1 wt %, more preferably greater than 0.2 wt %, more preferably greater than 0.5 wt %, more preferably greater than 1.0 wt %, and most preferably greater than 1.5 wt %, Most preferably the alkyl polyethoxy amide comprises PEG 4 rapeseed amide.

Preferably the alkyl ether sulphate is present in an amount of >12 wt %.

More preferably the metal salt is present in an amount of 0.1-5 wt %, more preferably 0.2-3 wt %, and most preferably about 2 wt %.

Preferably the metal salt comprises an alkali and/or alkaline metal halide. Preferred examples of alkali and/or alkaline metal halides include sodium and/or calcium chloride.

Most preferably the alkyl ether sulphate comprises sodium laureth sulphate.

DETAILED DESCRIPTION OF THE SECOND ASPECT OF THE INVENTION

More preferably the betaine surfactant is present in an amount of from 0.1-2 wt %, and most preferably about 0.6 wt %.

Alkyl betaines are known surfactants which are mainly produced by carboxyalkylation, preferably carboxymethylation of aminic compounds. Typical examples are the carboxymethylation products of hexyl methyl amine, hexyl dimethyl amine, octyl dimethyl amine, decyl dimethyl amine, dodecyl methyl amine, dodecyl dimethyl amine, dodecyl ethyl methyl amine, $C_{12/14}$ cocoalkyl dimethyl amine, myristyl dimethyl amine, cetyl dimethyl amine, stearyl dimethyl amine, stearyl ethyl methyl amine, oleyl dimethyl amine, $C_{16/18}$ tallow alkyl dimethyl amine and technical mixtures thereof. Alkyl amidobetaines which represent carboxyalkylation products of amidoamines are also suitable. Typical examples are reaction products of fatty acids containing 6 to 22 carbon atoms, namely caproic acid, caprylic acid, capric acid, lauric acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof, with N,N-dimethylaminoethyl amine, N,N-dimethylaminoproply amine, N,N-diethylaminoethyl amine and N,N-diethylaminoproply amine which are condensed with sodium chloroacetate.

Most preferably the betaine comprises cocoamidopropyl betaine.

More preferably the lactic acid is the lactic acid is present in an amount of from 0.2-5 wt %, more preferably 0.3-5 wt %, more preferably 0.4-5 wt % and most preferably from 2-5 wt %, e.g. about 2.75 wt %.

More preferably the polyhydric $C_2$-$C_6$ alcohol is present in an amount of 2-18 wt %, more preferably 6-17 wt %, more preferably 8-16 wt %, and most preferably from 10-15 wt %.

Most preferably the polyhydric $C_2$-$C_6$ alcohol comprises glycerol.

DETAILED DESCRIPTION

Surprisingly it has been found that the compositions of the invention achieve satisfactory cleaning and germ kill whilst avoiding issues caused by irritancy from these sulphur containing compounds, notably sulphur containing surfactants such as Sodium Laureth Sulfate (SLES). SLES is an inexpensive and very effective foaming agent. It has also been shown that SLES causes skin irritation. This is particularly significant, given the main preferred intimate use of the present invention. For this preferred use clearly it is surprisingly advantageous that irritation has been avoided.

In more detail it has been observed that the composition may be characterized in exhibiting at least a 1 $\log_{10}$ reduction of various microorganisms/bacteria, such as E Coli when tested according to the standardized test protocols of ASTM E2315-03 "Standard Guide for Assessment of Antimicrobial Activity Using a Time-Kill Procedure."

Antimicrobial Test Protocol:

A testing protocol according to ASTM E2315-03 "Standard Guide for Assessment of Antimicrobial Activity Using a Time-Kill Procedure" was used to evaluate antimicrobial efficacy against both Gram positive (*Staphylococcus aureus*) (ATCC 6538), Gram negative (*Escherichia coli*) (ATCC 10536) bacteria and the yeast *Candida albicans* (ATCC 10231). According to this protocol, first, the challenge cultures (18-24 hours) were prepared by suspension in tryptic sodium chloride, equilibrated to 20° C.-22° C. at room temperature. On the day of such testing, 5 ml sample of a composition product was combined with 4 ml ml of standardized hard water (~300 ppm $CaCO_3$) at room temperature (20° C.-22° C.) in a sterile vessel (e.g, test tube). Subsequently 1 ml of the test culture was added, which resulted in a 50% v/v dilution. The test tube was then vortexed for 5 seconds, and allowed to remain in contact for 60+/−5 seconds, immediately after which a 1 ml aliquot was withdrawn and added to a further tube containing 9 ml of a neutralizer. The neutralization was allowed to occur for 5 minutes, and thereafter serial tenfold dilutions using tryptic sodium chloride were plated, and incubated for 24-48 hours at 36+1° C. The inocula used were also serially diluted, plated and incubated for 24-48 hours at 36+1° C. Post-incubation the surviving colony-forming units (CFUs) of the challenge organisms were enumerated and $\log_{10}$ reduction values for each formulation tested were determined from one or more replicate samples, in the case of plurality of replicate samples the average results were reported.

pH

It is contemplated that certain preferred embodiments of the inventive formulations may also provide an antiseptic or sanitizing benefit which is aided due to the low pH of particularly preferred embodiments of the invention, particularly wherein the compositions are at a pH of 3.8-4.5.

Viscosity

The compositions of the first aspect of the invention are viscous and exhibit a viscosity of at least 500 cps at room temperature as measured using a Brookfield viscometer, Type 3 spindle at 12 rpm. Preferably the compositions of the first aspect of the invention exhibit viscosities in the range of at least about 500 cps as measured under these conditions. Yet more preferably the topical compositions of the invention exhibit a viscosity in the range of about 1000 to about 10,000 cps, yet more preferably from about 1500 to 7000 cps, and especially preferably from about 1500-4500 cps.

While the topical compositions disclosed herein find a primary use in application to the skin to provide a cleaning and an antimicrobial benefit and is contemplated as being provided in a dispenser for use in such a treatment, it is to be understood that this is not a limiting definition and that other forms and other uses of the present inventive composition, such as face lotion, milky lotion, cream, face cleansing cream, massage materials, liquid toilet soap, as well as in hair care products such as shampoo, rinse or other hair or scalp treatment are expressly contemplated as being within the scope of the present invention. It is to be further expressly understood that the compositions disclosed herein may be topically applied to the skin on any part of the body, including the skin on the face, neck, chest, back, arms, axilla, hands, legs, and scalp.

Optional Constituents

A sequestrant may optionally be present. The overall level of sequestrant present (when present) may be within the range of 0.1 to 10 wt %.

Particularly preferred sequesterants for use with the invention are iminodisuccinic acid or its salts and/or DTPA (diethylene triamine pentaacetic acid) such as Dequest 2066 (Trade Mark; product available from Solutia Inc., St Louis 6366-6760, USA), EDTA, and Dissolvine (GLDA/glutamate diacetate) EDG (Trade Mark; product available from Akzo Nobel, Gillingham, UK), The inventive compositions may optionally include further constituents useful in improving one or more aesthetic characteristics of the compositions or in improving one or more technical characteristics of the compositions. Exemplary further optional constituents include colouring agents, fragrances and fragrance solubilizers, viscosity modifying agents including one or more thickeners, pH adjusting agents and pH buffers including organic and inorganic salts, optical brighteners, opacifying agents, hydrotropes, and preservatives, as well as other optional constituents providing improved technical or aesthetic characteristics known to the relevant art. When present, the total amount of such one or more optional constituents present in the inventive compositions do not exceed about 10% wt., preferably do not exceed 5% wt, and most preferably do not exceed 2.5% wt.

These aspects and advantages of the invention are discussed in more detail hereinafter, particularly in reference to one or more of the examples set forth below.

EXAMPLES

Example 1—Base Formula and Antimicrobial Performance

This table demonstrates the impact on micro performance by total surfactant, lactic acid and salt concentration changes to the base gel body wash formula (E1). A passing formula is defined as one achieving at least 1 log kill against both *S. aureus* and *E. coli* when tested according to the standardized test protocols of ASTM E2315-03 "Standard Guide for Assessment of Antimicrobial Activity Using a Time-Kill Procedure." A 1 log kill against *C. albicans* is also preferred given its relevance in the intimate area.

| Raw Material | E1 | E2 | E3 | E4 | E5 |
|---|---|---|---|---|---|
| | | | % w/w | | |
| | Chemical composition | | | | |
| DI Water | 53.39 | 53.64 | 52.09 | 63.12 | 52.09 |
| Tetrasodium Glutamate Diacetate | 0.4 | 0.2 | 0.4 | 0.4 | 0.4 |
| Sodium Laureth Sulfate (70% active) | 12.16 | 11.55 | 12.16 | 12.16 | 12.16 |
| Sodium Laureth 11 Carboxylate | 4.85 | 4.61 | 4.85 | 4.85 | 4.85 |
| PEG 4 Rapeseedamide | 1.7 | 1.62 | 1.7 | 1.7 | 1.7 |
| Cocamidopropyl Betaine (35% active) | 4.25 | 4.03 | 4.45 | 4.25 | 4.45 |
| Glycerin | 14.25 | 10 | 10 | 5 | 10 |
| Fragrance | 0.25 | 0.15 | 0.15 | 0.1 | 0.15 |
| Extract | 0 | 0.1 | 0.1 | 0 | 0.1 |
| Benzoic acid, sorbic acid, benzyl alcohol | 1 | 0.6 | 0.6 | 1 | 0.6 |
| Lactic Acid (88% solution) | 2.5 | 2.5 | 2.5 | 1.75 | |
| Lactic Acid (50% solution) | | | | | 4.5 |
| Sodium Hydroxide (30% solution) | 0.5 | 1.25 | 1.25 | 0.84 | 1.25 |
| Sodium Chloride (20% solution) | 5 | 10 | 0 | 5 | 10 |
| Calcium Chloride (20% solution) | 0 | 0 | 10 | 0 | 0 |
| Formula pH | 4.18 | 4.30 | 4.19 | 4.20 | 4.19 |
| Antimicrobial Performance | Log Reduction | | | | |
| *S. aureus* | 4.01 | 1.62; | 4.3 | 0.03 | 4.48 |
| *E. coli* | >5 | 0.07; 0.59 | 3.8 | >5 | 4.96 |
| *C. albicans* | 1.04; 0.99 | | 1.82 | | 1.5 |
| *K. pneunomiae* | 3; 3.89 | — | — | 2.0; 1.5 | — |
| *B. Streptococcus* | | | | | 5.39 |
| *C. xerosis* | | | | | >4.56 |
| Overall micro performance | Pass | Fail | Pass | Fail | Pass |
| Comments | Base formula | Low surfactant | With 10% CaCl2 | Low lactic acid | 50% lactic acid |

The data demonstrates that reduction of the total surfactant system by 5% results in lower *E coli* performance based on example E2. In example E4, micro efficacy is also negatively impacted by reducing lactic acid to 1.75%. Example E3 demonstrates that positive efficacy is retained by substituting sodium chloride with calcium chloride. Example E5 demonstrates that positive efficacy is retained by substituting 38% lactic acid with 50% lactic acid. In fact, a 0.5 log increase in kill on *C. albicans* is noted. It is suspected that this benefit may come from the fact that more dilute solutions of lactic acid are richer in the monomer form of lactic acid which is more potent than the polymeric form.

TABLE A

| Ingredients with trade name | |
|---|---|
| Raw Material | Trade Name |
| Tetrasodium Glutamate Diacetate | Dissolvine GL 47 S |
| Sodium Laureth Sulfate | Texapon N70A |
| Sodium Laureth 11 Carboxylate | Akypo Soft 100 BVC |
| PEG 4 Rapeseedamide | Amidet N |
| Cocamidopropyl Betaine | Mackam 35 |
| Glycerin | Glycerin USP Kosher |
| Benzoic acid, sorbic acid, benzyl alcohol | Microcare SBB |
| Lactic Acid | Purac HiPure 90, Ultrapure 50 |

The E1, E3 and E5 formulations as described above have been found to:—

1 be mild to the skin and provide appropriate antimicrobial action providing at least 1 log reduction of certain germs/bacteria.

1 be mild to the skin and provide stable pH to the intimate skin over 28 days. (Demonstrated as no statistically significant change over 28 days).

1 provide moisturization to the skin. (Statistically significant ($p<0.05$) increase in moisturization of intimate area skin over 28 days. Further demonstrated as a statistically significant ($p<0.05$ compared to baseline) increase in moisturization of keratinized skin after 1 hour).

1 respect the natural balance of resident/commensal flora in the intimate area.

Example 2—Dermal Irritation or Sensitisation Study

The gel formulae E5 was placed in a clinical study to determine the dermal irritation and sensitisation potential following external contact with the skin on human subjects.

The study was performed on 104 healthy subjects, using application of semi-occlusive patches bearing the test products (diluted to 1%) to marked skin sites on the upper back (between the scapulae) for nine exposure periods of 24 hours during a 3-week induction phase. Skin sites were assessed for erythema, edema and other signs of irritancy approximately 48 hours following each application. Following approximately a 2 week rest period after the induction phase, semi-occlusive product challenge patches were applied for 24 hours to a previously untreated site on the lower back. Challenge sites were assessed for erythema, edema and other signs of irritancy 24, 48, and 72 hours after patch application for determination for sensitization potential.

No visible skin reactions were observed.

The study concluded that based on a test population of 104 subjects and under conditions of the study as described, the formula identified above did not demonstrate a potential for eliciting dermal irritation or sensitization, thus supporting that the formula is mild and gentle.

Example 3—Comparison of Inventive Feminine Gel Vs. Competitor Product

Kora is an intimate hygiene gel product containing a lactic acid/chamomile antimicrobial complex. However, when tested the low dosage of lactic acid in the Kora product does not provide sufficient anti-microbial efficacy to promote adequate hygiene of the intimate feminine area. See results below.

| Sample information | Lactic acid % active basis | Glycerin %, active basis | pH |
|---|---|---|---|
| Kora | 0.08 | 1.81 | 5.0-6.0 |
| Inventive formulation E5 | 2.25 | 10 | 4.19 |

| Sample information | *S. aureus* Log10 Reduction 60 sec | *E. coli* Log10 Reduction 60 sec |
|---|---|---|
| Kora | 0, 0, 0.02 (0) | 0, 0, 0 (0) |
| Inventive formulation E3 | (4.3) | (3.8) |

In addition, it was found that the Kora product (like many commercial intimate hygiene products) has a very low level of glycerine, which may not provide adequate moisturization benefits as compared to a gel according to the invention.

The inventive formulation demonstrated that the key to an effective antimicrobial benefit is the three surfactant systems with high amount of lactic acid synergy.

Example 4—Intimate Foam Cleanser

Intimate Foam wash is another format of well received feminine products. Lactic acid was used again as an antimicrobial active in the foam formulas. The formulations contain a lower amount of total surfactant versus the prior gel examples and further contain a higher level of lactic acid to help balance the micro efficacy of the formulation. The formulations are water thin to allow for use with either a foam pump package or a squeeze foam dispenser.

A passing formula for foam is also defined as one achieving at least 1 log kill against both *S. aureus* and *E. coli* when tested according to the standardized test protocols of ASTM E2315-03 "Standard Guide for Assessment of Antimicrobial Activity Using a Time-Kill Procedure." A 1 log kill against *C. albicans* is also preferred given its relevance in the intimate area.

| | Intimate Foam | | | |
|---|---|---|---|---|
| Raw Material | E6 | E11 | E12 | E13 |
| | % w/w | | | |
| | Chemical composition | | | |
| DI Water | 87.97 | 87.47 | 93.07 | 85.9 |
| Tetrasodium Glutamate Diacetate | 0.4 | 0.4 | 0.4 | 0.4 |
| Sodium Laureth 11 Carboxylate | 0 | 0 | 0 | 2 |
| Cocamidopropyl Betaine (30%) | 2 | 2 | 0.5 | 2 |
| Glycerin | 5 | 5 | 1 | 5 |
| Benzoic acid, sorbic acid, benzyl alcohol | 1 | 1 | 1 | 1 |
| Lactic Acid (based on 100% active) | 2.25 | 2.75 | 2.75 | 2.25 |
| 50% Sodium Hydroxide | 1.38 | 1.38 | 1.28 | 1.45 |
| pH | 4.2 | 4.2 | 4.18 | 4.2 |
| Germ kill efficacy | Log reduction | | | |
| *S. aureus* | 0.65 | 1.32, 1.48 | 2.12, 1.50 | 0 |
| *E. coli* | >5.59, | >5.35 | 5.36, 4.73 | 1.91, 2.47 |
| *C. albicans* | — | 0.04 | — | — |
| Over micro performance | Fail | Pass | Pass | Fail |
| Summary | Low surfactant | High lactic acid level | High lactic level, low betaine | Low surfactant, low lactic |

Example 5—Feminine Hygiene Wash In-Use Tolerance and Microbiome Study

Following a 7 day pre-study conditioning period with a pH 5.6 Shower Gel product, 34 healthy female subjects used the test product (Formula E5) to wash the external intimate area at least once per day for 28 days, with assessments at baseline (Day 0) and Days 14 and 28. Tolerance assessments of skin dryness, erythema, oedema, desquamation, itching (verbal questioning of subjects, visual assessment for scratch marks), burning (verbal questioning of subjects), stinging (verbal questioning of subjects) and other clinical signs of irritancy of the intimate area were carried out by a gynaecologist. Subjects provided subjective tolerance assessments at baseline (Day 0) and Days 14 and 28.

Skin pH measurements of the mid-labium majus were taken with a Multi Probe Adaptor System (MPA System) (Courage & Khazaka GmbH) using the skin-pH meter PH 905 probe at baseline (Day 0) and Days 14 and 28. Skin hydration and moisturization measures were taken with a Corneometer® CM 825 (Courage & Khazaka GmbH) using a Multi-Probe Adaptor (MPA) 6 with Corneometer probe after the subject had remained in climate controlled conditions (acclimatized 22±2° C. and 35-55% RH) for 20 minutes. Skin hydration of the groin area was measured using a Corneometer at baseline (Day 0) and Days 14 and 28 to assess longer lasting benefits. Skin moisturization of the upper inner leg area before and at two time points after application of test product by the study technician were measured using a Corneometer at baseline (T-0 h), T-0 post wash (immediately after test product wash) and T-1 h after application of test product wash to assess single use/short term benefits.

Microbiological samples were taken from the mid-labium majus area via a liquid cup scrub method at baseline (Day 0) and Days 14 and 28. A glass cylinder was pressed (approx. 4 cm$^2$ in area) to firmly make contact with the skin exerting adequate pressure to prevent leaking of liquid during collection. 1 ml of 0.1% detergent solution (75 mM phosphate buffer containing 0.1% (v/v) Triton X-100 (full strength wash fluid) buffered to a pH between 7.5-8.0) was pipetted into the sterile glass cylinder circumscribing an area of about 3.0 cm$^2$ and the skin surface was carefully rubbed as evenly as possible with a blunted sterile glass rod (scrubbing device), applying moderate constant pressure for 1 min. Samples were boiled at 96 C for 10 minutes to sterilize, packaged in dry ice and shipped for microbial diversity analysis.

Thirty six (36) subjects were enrolled on the study. Two (2) subjects withdrew leaving thirty-four (34) subjects completing the study, and their microbiome data were included in the analysis. Subjects were aged between 19 and 55 years (mean 36.61, SD 11.28). Twelve subjects (33.3%) were aged between 18-29; 13 (36.1%) subjects were aged between 30-44 and 11 (30.6%) subjects were aged between 45-55.

Dermal irritancy scores (mean total scores) based on a 5-point scale 0=none, 0.5=very slight, 1=slight, 2=moderate, 3=severe, increased from 0.01 at Day 0 to 0.12 at Day 14 and 0.13 at Day 28. The mean within subject change from baseline total irritancy scores at Day 14 and 28 were 0.10 and 0.12 respectively meeting acceptable tolerance criteria. The Overall Tolerance Rating made by the Gynaecologist after 28 days of use was: "the test product was well tolerated by most subjects".

The skin pH (overall population) of the external intimate area at Day 0 was 5.88. At Day 14 the pH decreased very slightly to 5.87 and at Day 28 to 5.85. The mean within subject change from baseline pH was −0.01 at Day 14 and −0.03 at Day 28. Analysis showed no significant differences between the time points; p-value 0.992 between D-0 & D-14, p-value 0.883 between D-0 & D-28 and p-value 0.933 between D-14 & D-28; all much higher than the 0.05 associated with the 95% confidence level. Statistical analysis confirms no significant differences (overall population) in skin pH of external (vulva) area over time with product use. Skin hydration, measured in the groin area, by the mean Corneometer scores was 39.14 at Day 0. At Day 14 this increased to 45.97 and at Day 28 increased to 48.86. Skin hydration increased over the 28 day duration of the study. Analysis showed a statistically significant increase (p<0.05) in skin hydration at D-14 and D-28 (p=<0.0001).

Skin moisturization, measured in the upper inner leg area by the mean Corneometer scores, for the test product was statistically significantly greater at T-1 hour (p=<0.0001) versus baseline (34.43 vs 29.98).

To perform the microbial diversity analysis, 16s rRNA sequences were amplified, sequenced and OTUs (operational taxonomic units) were assigned to each sequence based on the NCBI database.

Diversity was examined from two perspectives. First, overall richness (i.e., number of distinct organisms present within the microbiome), was expressed as the number of operational taxonomic units (OTUs), and was quantified using the Chao1 richness estimator. Secondly, overall diversity (which is determined by both richness and evenness, the distribution of abundance among distinct taxa) was expressed as Shannon Diversity.

Measures of diversity were screened for group differences using an analysis of variance (ANOVA). Results (shown below) indicates that the gel wash formulation tested has no significant (p>0.05) impact on species richness and diversity at any of the time points assessed for either bacteria or fungi of the external intimate skin microbiome. In fact it was shown to stabilize the intimate skin microbiome.

TABLE B

Bacterial alpha diversity metrics comparing time points:

|  | Day 0 (n = 34) | Day 14 (n = 34) | Day 28 (n = 34) |
| --- | --- | --- | --- |
| Observed OTUs | 222.74 | 176.47 | 186.56 |
| Chao1 Richness | 246.64 ± 9.64 | 201.55 ± 10.83 | 210.2 ± 10.16 |
| Shannon Diversity | 2.58 | 2.37 | 2.36 |

TABLE C

Results of the ANOVA, testing for differences in Chao1 Richness among time points:

|  | Df | Sum Sq | Mean Sq | F value | Pr(>F) |
| --- | --- | --- | --- | --- | --- |
| Time | 2 | 38932.63 | 19466.32 | 2.01 | 0.1400 |
| Residuals | 99 | 960760.90 | 9704.66 |  |  |

TABLE D

Results of the ANOVA, testing for differences in Shannon diversity among time.

|  | Df | Sum Sq | Mean Sq | F value | Pr(>F) |
| --- | --- | --- | --- | --- | --- |
| Time | 2 | 1.08 | 0.54 | 1.19 | 03097 |
| Residuals | 99 | 44.90 | 0.45 |  |  |

TABLE E

Fungal alpha diversity metrics comparing time points:

|  | Day 0 (n = 16) | Day 14 (n = 12) | Day 28 (n = 13) |
| --- | --- | --- | --- |
| Observed OTUs | 5.06 | 4.75 | 186.56 |
| Chao1 Richness | 5.08 ± 0.08 | 4.75 ± 0.04 | 6.31 ± 0.05 |
| Shannon Diversity | 0.37 | 0.37 | 0.48 |

TABLE F

Results of the ANOVA, testing for differences in Chao1 Richness among time.

|  | Df | Sum Sq | Mean Sq | F value | Pr(>F) |
| --- | --- | --- | --- | --- | --- |
| Time | 2 | 17.44 | 8.72 | 0.90 | 0.4169 |
| Residuals | 38 | 369.97 | 9.74 |  |  |

TABLE G

Results of the ANOVA, testing for differences in Shannon diversity among time.

|  | Df | Sum Sq | Mean Sq | F value | Pr(>F) |
|---|---|---|---|---|---|
| Time | 2 | 0.11 | 0.06 | 0.44 | 0.6469 |
| Residuals | 38 | 4.92 | 0.13 | | |

IN CONCLUSION

The gel wash when used by women on the external genital area at least once per day over a 4 week period (28 days), demonstrated acceptable tolerance, did not significantly change the skin pH in the external vulvar area and provided significant skin hydration and moisturization benefits. Furthermore microbiome analysis of the external vulvar area showed the formula had no significant impact on species richness and diversity for bacteria or fungi, with a stabilizing effect on the microbiome.

The invention claimed is:

1. A personal wash composition comprising:
   from 1 wt % to 3 wt % betaine surfactant;
   from 2 wt % to 5.0 wt % lactic acid;
   from 10 wt % to 15 wt % glycerol;
   from 2 wt % to 7 wt % alkyl polyethoxy carboxylate;
   from 1 wt % to 3 wt % alkyl polyethoxy amides;
   greater than 8 wt % alkyl ether sulphate;
   water;
   a pH of 3.8-4.5;
   10-20 wt % total surfactant; and
   0.1 to 10 wt % metal salt,
   wherein the personal wash composition provides an effective antimicrobial benefit against fungi, gram positive bacteria, and gram negative bacteria,
   wherein the alkyl polyethoxy carboxylate is of the formula $RO(CH_2CH_2O)_kCH_2COO^-M^+$;
   wherein R is a $C_8$-$C_{22}$ alkyl;
   wherein k is an integer from 0 to 20; and
   wherein M is a soluble salt-forming cation; and
   wherein the alkyl polyethoxy amides are of the formula $RO(CH_2CH_2O)_kCH_2CONH_2$ wherein R is a $C_8$-$C_{22}$ alkyl, and k is an integer from 0 to 20.

2. The composition according to claim 1, wherein the alkyl polyethoxy carboxylate is present in an amount of about 4.8 wt %.

3. The composition according to claim 2, wherein in the alkyl polyethoxy carboxylate, R is a $C_{12}$ alkyl, K is 11, and M is Na.

4. The composition according to claim 1, wherein the betaine surfactant is present in an amount of about 1.3 wt %.

5. The composition according to claim 1, wherein the betaine comprises cocoamidopropyl betaine.

6. The composition according to claim 1, wherein the alkyl polyethoxy amide comprises PEG 4 rapeseed amide.

7. The composition according to claim 1, wherein the metal salt is present in an amount of from 0.1-5 wt %.

8. The composition according to claim 1, wherein the metal salt comprises one or both of an alkali and an alkaline metal halide.

9. The composition according to claim 1, wherein the alkyl ether sulphate comprises sodium laureth sulphate.

10. A method for providing a germicidal benefit to a topical surface comprising:
    contacting a topical surface with the composition according to claim 1; and
    providing an effective germicidal benefit against fungi, gram-positive and gram-negative bacteria if the topical surface, prior to contact with the composition, had the presence of one or more of fungi, gram-positive and gram-negative bacteria.

11. A method for providing a germicidal benefit to a dermal surface comprising:
    contacting a dermal surface with the composition according to claim 1; and
    providing an effective germicidal benefit against undesired pathogens if the dermal surface, prior to contact with the composition, had the presence of one or more undesired pathogens, while not upsetting or disrupting the natural balance of microflora or microbiome on the dermal surface.

12. A method for stabilizing the pH of a surface comprising contacting a surface upon which the presence of one or more undesired pathogens are known or suspected, with the composition according to claim 1.

13. A method for stabilizing microbiome or microflora of a surface comprising contacting a surface upon which the presence of one or more undesired pathogens are known or suspected, with the composition according to claim 1.

14. A method of moisturizing a surface comprising contacting a surface upon which the presence of one or more undesired pathogens are known or suspected, with the composition according to claim 1.

15. A personal wash composition comprising:
    sodium laureth carboxylate in an amount of about 4.8 wt %;
    betaine surfactant in an amount of about 1.3 wt %;
    lactic acid in an amount of about 2 wt % to 5 wt % wt %;
    glycerol in an amount of from 10-15 wt %;
    rapeseed amide in an amount of from 1-3 wt %;
    sodium laureth sulfate in an amount of greater than 8 wt %;
    10-20 wt % total surfactant; and
    sodium chloride in an amount of about 2 wt %,
    wherein the composition has a pH of 4 to 4.4.

16. The composition according to claim 1, wherein the composition has a pH of 4 to 4.4.

* * * * *

UNITED STATES PATENT AND TRADEMARK OFFICE
CERTIFICATE OF CORRECTION

PATENT NO. : 11,896,698 B2
APPLICATION NO. : 15/763920
DATED : February 13, 2024
INVENTOR(S) : Jessica Wilson et al.

It is certified that error appears in the above-identified patent and that said Letters Patent is hereby corrected as shown below:

In the Specification

Column 7, Line 54: Delete "38%" and replace with -- 88% --

Column 10, Line 3: Delete "water thin" and replace with -- water-thin --

Signed and Sealed this
Nineteenth Day of March, 2024

Katherine Kelly Vidal
*Director of the United States Patent and Trademark Office*